United States Patent
Evans et al.

(10) Patent No.: US 10,526,300 B2
(45) Date of Patent: Jan. 7, 2020

(54) PROCESSES AND SYSTEMS FOR REMOVING IODIDE IMPURITIES FROM A RECYCLE GAS STREAM IN THE PRODUCTION OF ETHYLENE OXIDE

(71) Applicant: SHELL OIL COMPANY, Houston, TX (US)

(72) Inventors: Wayne Errol Evans, Richmond, TX (US); Jesse Raymond Black, Houston, TX (US); Michael Francis Lemanski, Houston, TX (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 16/061,770

(22) PCT Filed: Dec. 13, 2016

(86) PCT No.: PCT/EP2016/080759
§ 371 (c)(1),
(2) Date: Jun. 13, 2018

(87) PCT Pub. No.: WO2017/102706
PCT Pub. Date: Jun. 22, 2017

(65) Prior Publication Data
US 2018/0370935 A1    Dec. 27, 2018

(30) Foreign Application Priority Data
Dec. 15, 2015    (EP) ..................................... 15200275

(51) Int. Cl.
*C07D 301/32*    (2006.01)
*B01D 53/70*    (2006.01)
(Continued)

(52) U.S. Cl.
CPC ....... *C07D 301/32* (2013.01); *B01D 53/0423* (2013.01); *B01D 53/70* (2013.01);
(Continued)

(58) Field of Classification Search
CPC .... B01D 53/04; B01D 53/0423; B01D 53/96; B01D 53/02; B01D 53/70; B01D 53/8662;
(Continued)

(56) References Cited

U.S. PATENT DOCUMENTS

| 2,289,063 A | 7/1942 | Ocon et al. |
| 4,048,096 A | 9/1977 | Bissot |

(Continued)

FOREIGN PATENT DOCUMENTS

| DE | 202012012866 U1 | 2/2014 |
| EP | 0776890 A2 | 6/1997 |

(Continued)

OTHER PUBLICATIONS

Grant et al , Grant & Hach's Chemical Dictionary, MacGraw-Hill Book Co. 1987, p. 433. (Year: 1987).*

(Continued)

*Primary Examiner* — Taylor V Oh
(74) *Attorney, Agent, or Firm* — James D. Carruth

(57) ABSTRACT

Processes for reducing the amount of a gaseous iodide-containing impurity present in a recycle gas stream used in the production of ethylene oxide, in particular alkyl iodide and vinyl iodide impurities, are provided. Processes for producing ethylene oxide, ethylene carbonate and/or ethylene glycol, and associated reaction systems are similarly provided.

15 Claims, 4 Drawing Sheets

(51) Int. Cl.
  *B01D 53/04* (2006.01)
  *B01D 53/96* (2006.01)
  *C07D 301/10* (2006.01)
  *C07D 303/04* (2006.01)

(52) U.S. Cl.
  CPC .......... *B01D 53/96* (2013.01); *C07D 301/10* (2013.01); *C07D 303/04* (2013.01); *B01D 2253/104* (2013.01); *B01D 2253/106* (2013.01); *B01D 2253/1122* (2013.01); *B01D 2257/2068* (2013.01)

(58) Field of Classification Search
  CPC .......... B01D 53/1475; B01D 2253/112; B01D 2253/102; B01D 2253/104; B01D 2253/106; B01D 2253/1122; B01D 2253/1023; B01D 2255/106; C07D 301/10; C07D 301/32; C07D 301/08; C07D 303/04; C07C 317/38; C07C 29/106; C07C 17/38; C07C 21/17; C07C 19/07; C07C 31/202; Y02P 20/154; Y02P 20/152
  USPC .......................................................... 549/542
  See application file for complete search history.

(56) References Cited

U.S. PATENT DOCUMENTS

| | | |
|---|---|---|
| 4,761,394 A | 8/1988 | Lauritzen |
| 4,766,105 A | 8/1988 | Lauritzen |
| 4,789,528 A | 12/1988 | Owen et al. |
| 5,179,057 A | 1/1993 | Bartley |
| 5,189,004 A | 2/1993 | Bartley |
| 5,380,697 A | 1/1995 | Matusz et al. |
| 5,739,075 A | 4/1998 | Matusz |
| 6,040,467 A | 3/2000 | Papavassiliou et al. |
| 6,368,998 B1 | 4/2002 | Lockemeyer |
| 6,656,874 B2 | 12/2003 | Lockemeyer |
| 7,030,056 B2 | 4/2006 | Birke et al. |
| 7,193,094 B2 | 3/2007 | Chipman et al. |
| 7,425,647 B2 | 9/2008 | Lemanski et al. |
| 8,546,592 B2 | 10/2013 | Evans et al. |
| 8,921,586 B2 | 12/2014 | Matusz |
| 8,932,979 B2 | 1/2015 | Matusz et al. |
| 2006/0070918 A1 | 4/2006 | Seapan et al. |
| 2008/0281118 A1 | 11/2008 | Matusz |
| 2009/0143627 A1* | 6/2009 | Van Kruchten ....... C07C 29/106 568/860 |
| 2011/0034710 A1 | 2/2011 | Matusz |
| 2017/0291119 A1 | 10/2017 | Wilkinson et al. |

FOREIGN PATENT DOCUMENTS

| | | |
|---|---|---|
| EP | 2279182 A1 | 2/2011 |
| GB | 2107712 A | 5/1983 |
| WO | 9908790 A1 | 2/1999 |
| WO | 9908791 A1 | 2/1999 |
| WO | 2008144402 A2 | 11/2008 |
| WO | 2009021830 A1 | 2/2009 |
| WO | 2009140319 A1 | 11/2009 |
| WO | 2016001348 A1 | 1/2016 |
| WO | 2017102694 A1 | 6/2017 |
| WO | 2017102698 A1 | 6/2017 |
| WO | 2017102701 A1 | 6/2017 |

OTHER PUBLICATIONS

International Search Report and Written Opinion received for PCT Patent Application No. PCT/EP2016/080744, dated Mar. 14, 2017, 12 pages.
International Search Report and Written Opinion received for PCT Patent Application No. PCT/EP2016/080749, dated Feb. 17, 2017, 8 pages.
International Search Report and Written Opinion received for PCT Patent Application No. PCT/EP2016/080752, dated Apr. 4, 2017, 9 pages.
International Search Report and Written Opinion received for PCT Patent Application No. PCT/EP2016/080759, dated Apr. 4, 2017, 9 pages.
Evans et al., "Industrial Epoxidation Processes", Industrial Epoxidation Processes, Encyclopedia of Catalysis (Wiley-Interscience), 2003, vol. 3, p. 246-264.
Brunauer et al., "Adsorption of Gases in MultiMolecular Layers", Journal of American Chemical Society, Feb. 1938, vol. 60, Issue No. 2, pp. 309-319.
Kirk-Othmer, Encyclopedia of Chemical Technology, 4th Edition, vol. 9, pp. 915-959.

* cited by examiner

PROCESSES AND SYSTEMS FOR REMOVING IODIDE IMPURITIES FROM A RECYCLE GAS STREAM IN THE PRODUCTION OF ETHYLENE OXIDE

CROSS REFERENCE TO RELATED APPLICATIONS

This is a national stage application of International application No. PCT/EP2016/080759, filed 13 Dec. 2016, which claims benefit of priority of European application No. 15200275.4, filed 15 Dec. 2015.

FIELD OF THE INVENTION

The present invention relates to a process and reaction system for the preparation of ethylene oxide, ethylene carbonate and/or ethylene glycol from ethylene.

BACKGROUND

Monoethylene glycol is used as a raw material in the manufacture of polyester fibres, polyethylene terephthalate (PET) plastics and resins. It is also incorporated into automobile antifreeze liquids. Ethylene carbonate is typically used as a solvent.

Monoethylene glycol can be commercially prepared from ethylene oxide by various known methods. These methods, although varied, all generally involve a two-stage reaction system, wherein ethylene is first converted to ethylene oxide, which is then converted to ethylene glycol. In most industrial-scale glycol production operations, the process for the production and recovery of ethylene oxide is integrated with the process for the production of ethylene glycol to maximize energy utilization and reduce costs.

In the first stage, ethylene oxide is typically produced by reacting ethylene with air or elemental oxygen in the presence of a suitable catalyst, such as a silver-based epoxidation catalyst, and often in the presence of organic moderators, such as organic halides, in an epoxidation reactor. (see Kirk Othmer's Encyclopedia of Chemical Technology, $4^{th}$ edition, Vol. 9, pages 923-940). This reaction generally occurs at pressures of 10-30 bar and temperatures of 200-300° C., and produces an epoxidation reaction product comprising ethylene oxide, unreacted reactants (such as ethylene and oxygen), various impurities (such as aldehyde impurities, including formaldehyde and acetaldehyde) and optionally other gases and/or by-products (such as nitrogen, argon, methane, ethane, water and/or carbon dioxide).

In the second stage, ethylene oxide is converted to ethylene glycol by one of several methods. In one well known method, the epoxidation reaction product from the epoxidation reactor is supplied to an ethylene oxide absorber, along with a recirculating absorbent solution, typically referred to as "lean absorbent", to absorb the ethylene oxide from the epoxidation reaction product. The ethylene oxide absorber produces an aqueous product stream comprising ethylene oxide, commonly referred to as "fat absorbent", which is then supplied to an ethylene oxide stripper, wherein steam is usually introduced counter-currently to separate the ethylene oxide as a vapor stream. The separated ethylene oxide is withdrawn at or near the top of the ethylene oxide stripper, as a more concentrated aqueous ethylene oxide stream, while an aqueous stream withdrawn from the ethylene oxide stripper as bottoms is typically recirculated to the ethylene oxide absorber for reuse as lean absorbent. The aqueous ethylene oxide stream withdrawn from the ethylene oxide stripper is then further reacted to provide ethylene glycol, either by direct hydrolysis in a hydrolysis reactor (i.e., by thermally reacting ethylene oxide with a large excess of water) or alternatively, by reacting the ethylene oxide with carbon dioxide in a carboxylation reactor in the presence of a carboxylation catalyst to produce ethylene carbonate. The ethylene carbonate may then be supplied, along with water, to a hydrolysis reactor and subjected to hydrolysis in the presence of a hydrolysis catalyst to provide ethylene glycol. Direct hydrolysis of ethylene oxide typically produces a glycol product of approximately 90-92 wt. % monoethylene glycol (MEG) (with the remainder being predominately diethylene glycol (DEG), some triethylene glycol (TEG), and a small amount of higher homologues), whereas the reaction via the ethylene carbonate intermediary typically produces a glycol product in excess of 99 wt. % MEG.

Efforts have been made to simplify the process for obtaining ethylene glycol from ethylene oxide, reducing the equipment that is required and reducing the energy consumption. For example, GB 2107712 describes a process for preparing monoethylene glycol wherein the gases from the epoxidation reactor are supplied directly to a reactor wherein ethylene oxide is converted to ethylene carbonate or to a mixture of ethylene glycol and ethylene carbonate.

Similarly, EP 0776890 describes a process wherein the gases from the epoxidation reactor are supplied to an ethylene oxide absorber, wherein the absorbing solution mainly contains ethylene carbonate and ethylene glycol. The ethylene oxide in the absorbing solution is supplied to a carboxylation reactor and allowed to react with carbon dioxide in the presence of a carboxylation catalyst, such as an iodide-containing carboxylation catalyst. The ethylene carbonate in the absorbing solution is subsequently supplied, with the addition of water, to a hydrolysis reactor and subjected to hydrolysis in the presence of a hydrolysis catalyst, such as an alkali metal hydroxide.

EP 2178815 describes a reactive absorption process for preparing monoethylene glycol, wherein the gases from the epoxidation reactor are supplied to an absorber and the ethylene oxide is contacted with lean absorbent comprising at least 20 wt. % water in the presence of one or more catalysts that promote carboxylation and hydrolysis and the majority of the ethylene oxide is converted to ethylene carbonate or ethylene glycol in the absorber.

In each of these cases, a recycle gas stream containing gases that are not absorbed by the recirculating absorbent stream will be produced from the ethylene oxide absorber. Typically, at least a portion of this recycle gas stream is treated in a carbon dioxide absorption column and then recombined with any portion of the recycle gas stream bypassing the carbon dioxide absorption column. The combined gases are then recycled to the epoxidation reactor.

However, it has been found that in those processes where the carboxylation reaction is performed in the ethylene oxide absorber using an iodide-containing carboxylation catalyst, decomposition materials and side products may be present in the recycle gas stream and/or in the fat absorbent stream. Examples of such decomposition materials and side products include gaseous iodide-containing impurities, such as alkyl iodides (e.g., methyl iodide, ethyl iodide, etc.) and vinyl iodide.

The silver-based epoxidation catalysts typically used in an epoxidation reactor are susceptible to catalyst poisoning, in particular, poisoning by gaseous iodide-containing impurities, such as alkyl iodides and vinyl iodide. Catalyst poisoning impacts the epoxidation catalyst performance, in particular the selectivity and/or the activity, and shortens the length of time the epoxidation catalyst can remain in the epoxidation reactor before it becomes necessary to exchange the catalyst with fresh catalyst. Accordingly, it is desirable to remove such catalyst poisons as much as is practicable from the recycle gas stream before it comes into contact with the epoxidation catalyst. For example, the use of a purification zone or a guard bed upstream of an epoxidation reactor is disclosed in EP 2285795, EP 2279182 and EP 2155375.

The present inventors have found that the sensitivity of epoxidation catalysts to certain gaseous iodide-containing impurities, particularly alkyl iodides and vinyl iodide, is even greater than previously expected. The present inventors have, therefore, sought to provide improved guard bed systems and improved processes to remove certain gaseous iodide-containing impurities from a recycle gas stream in the manufacture of ethylene oxide, ethylene carbonate and/or ethylene glycol.

SUMMARY

In accordance with one aspect, a process for producing ethylene oxide is provided, the process comprising:

contacting at least a portion of a recycle gas stream comprising an alkyl iodide impurity and a vinyl iodide impurity with a first guard bed material to yield a partially treated recycle gas stream, wherein the first guard bed material comprises a first support material, and deposited on the first support material, silver in an amount of from 2% to 10% by weight;

contacting at least a portion of the partially treated recycle gas stream with a second guard bed material to yield a treated recycle gas stream, wherein the second guard bed material comprises a second support material, palladium and gold; and contacting an epoxidation feed gas comprising ethylene, oxygen and at least a portion of the treated recycle gas stream with an epoxidation catalyst to yield an epoxidation reaction product comprising ethylene oxide.

In accordance with another aspect, a process for producing ethylene carbonate and/or ethylene glycol is provided, the process comprising:

contacting at least a portion of a recycle gas stream comprising an alkyl iodide impurity and a vinyl iodide impurity with a first guard bed material to yield a partially treated recycle gas stream, wherein the first guard bed material comprises a first support material, and deposited on the first support material, silver in an amount of from 2% to 10% by weight;

contacting at least a portion of the partially treated recycle gas stream with a second guard bed material to yield a treated recycle gas stream, wherein the second guard bed material comprises a second support material, palladium and gold;

contacting an epoxidation feed gas comprising ethylene, oxygen and at least a portion of the treated recycle gas stream with an epoxidation catalyst to yield an epoxidation reaction product comprising ethylene oxide; and contacting at least a portion of the epoxidation reaction product comprising ethylene oxide with lean absorbent in the presence of an iodide-containing carboxylation catalyst to yield a fat absorbent stream comprising ethylene carbonate and/or ethylene glycol and the recycle gas stream comprising the alkyl iodide impurity and the vinyl iodide impurity.

Further, in accordance with yet another aspect, a reaction system for the production of ethylene carbonate and/or ethylene glycol is provided, the reaction system comprising:

a recycle gas loop fluidly connected to a source of ethylene and oxygen;

an epoxidation reactor comprising an epoxidation catalyst, an inlet, and an outlet, wherein the inlet of the epoxidation reactor is fluidly connected to the recycle gas loop;

an ethylene oxide absorber comprising an iodide-containing carboxylation catalyst, an inlet, and an outlet, wherein the outlet of the epoxidation reactor is fluidly connected to the inlet of the ethylene oxide absorber, the outlet of the ethylene oxide absorber is fluidly connected to the recycle gas loop, and the ethylene oxide absorber is configured to produce a recycle gas stream comprising a vinyl iodide impurity and an alkyl iodide impurity and a fat absorbent stream comprising ethylene carbonate and/or ethylene glycol;

a first guard bed system comprising an inlet, an outlet and one or more guard bed vessels comprising a first guard bed material that comprises a first support material, and deposited on the first support material, silver in an amount of from 2% to 10% by weight, wherein the inlet of the first guard bed system is fluidly connected to the recycle gas loop, and the first guard bed material is configured to remove at least a portion of the alkyl iodide impurity from at least a portion of the recycle gas stream to yield a partially treated recycle gas stream; and a second guard bed system comprising an inlet, an outlet and one or more guard bed vessels comprising a second guard bed material that comprises a second support material, palladium and gold, wherein the inlet of the second guard bed system is fluidly connected to the outlet of the first guard bed system, the outlet of the second guard bed system is fluidly connected to the recycle gas loop, and the second guard bed material is configured to remove at least a portion of the vinyl iodide impurity from at least a portion of the partially treated recycle gas stream.

BRIEF DESCRIPTION OF THE DRAWINGS

Some specific example embodiments of the disclosure may be understood by referring, in part, to the following description and the accompanying drawings.

Figure 1:
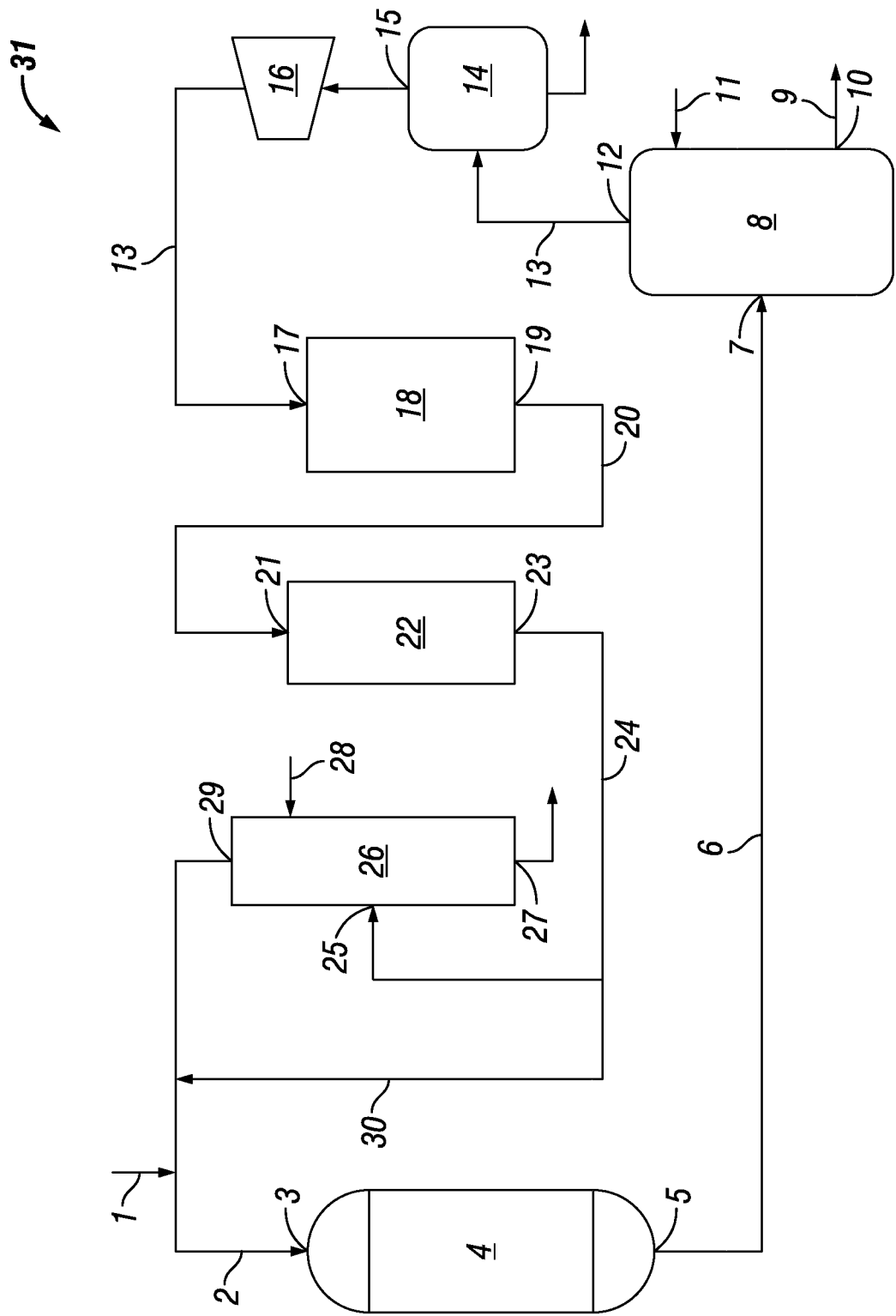
FIGS. 1-4 are schematic illustrations showing exemplary embodiments of the present disclosure.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DETAILED DESCRIPTION

It has been found that when ethylene oxide is catalytically reacted in the ethylene oxide absorber in the presence of an iodide-containing carboxylation catalyst, then gaseous iodide-containing impurities may be formed which exit the ethylene oxide absorber with the recycle gas stream. These gaseous iodide-containing impurities, particularly alkyl iodides and vinyl iodide, can poison the epoxidation catalyst in the epoxidation reactor, even in minute quantities.

Treating the recycle gas stream by contacting the stream with a guard bed material capable of at least partially absorbing such iodide-containing impurities can reduce the amount of such impurities in the recycle gas stream and thus protect the performance of the epoxidation catalyst, in particular the selectivity and/or activity of the catalyst, as well as the duration of time the epoxidation catalyst can remain in the epoxidation reactor before it becomes necessary to exchange the catalyst with fresh epoxidation catalyst.

Accordingly, described herein are processes and associated systems for producing ethylene oxide, ethylene carbonate and/or ethylene glycol wherein a recycle gas stream comprising an alkyl iodide impurity, such as methyl iodide and/or ethyl iodide, and a vinyl iodide impurity is contacted with a first guard bed material, which comprises silver in an amount of from 2% to 10% by weight deposited on a first support material, to reduce the amount of the alkyl iodide impurity present in the recycle gas stream and yield a partially treated recycle gas stream. The partially treated recycle gas stream is then contacted with a second guard bed material, which comprises a second support material, palladium and gold, to reduce the amount of the vinyl iodide impurity present in the partially treated recycle gas stream and yield a treated recycle gas stream.

By using the processes and systems disclosed herein, the amount of gaseous iodide-containing impurities present in a recycle gas stream are reduced to the very low levels the present inventors have now found to be required for the performance of the epoxidation catalyst to remain substantially unaffected by its presence. In particular, the amount of alkyl iodide present in a partially treated recycle gas stream is preferably no more than 6 ppbv, more preferably no more than 5 ppbv, even more preferably no more than 3 ppbv, even more preferably no more than 2 ppbv, and most preferably no more than 1 ppbv. Further, the amount of vinyl iodide present in a treated recycle gas stream is preferably no more than 20 ppbv, preferably no more than 15 ppbv, preferably no more than 10 ppbv, more preferably no more than 5 ppbv, even more preferably no more than 4 ppbv, even more preferably no more than 3 ppbv, and most preferably no more than 1 ppbv. Similarly, the total amount of alkyl iodide and vinyl iodide present in a treated recycle gas stream supplied to the epoxidation reactor is preferably no more than 26 ppbv, preferably no more than 20 ppbv, preferably no more than 16 ppbv, preferably no more than 13 ppbv, preferably no more than 10 ppbv, more preferably no more than 7 ppbv, even more preferably no more than 5 ppbv, most preferably no more than 2 ppbv.

Reference is made to FIG. 1, which is a schematic view of a reaction system (31) for the production of ethylene carbonate and/or ethylene glycol, according to an embodiment of the present disclosure. Reaction system (31) generally comprises epoxidation reactor (4), ethylene oxide absorber (8), first guard bed system (18), second guard bed system (22) and carbon dioxide absorber (26). It will be clear to the skilled person, that as schematic diagrams these figures do not show all necessary inputs, outputs, recycle streams, etc. that may be present in the reaction system. Furthermore, in the figures herein, as will be appreciated, elements can be added, exchanged, and/or eliminated so as to provide any number of additional embodiments and the sequence in which various feed components are introduced into the process and their respective points of introduction, as well as the flow connections, may be varied from that depicted. In addition, as will be appreciated, the proportion and the relative scale of the elements provided in the figure are intended to illustrate the embodiments of the present disclosure, and should not be taken in a limiting sense.

As shown in FIG. 1, epoxidation feed gas (2) is supplied to epoxidation reactor (4) via an inlet, such as inlet (3), which is in fluid communication with the recycle gas loop. Components of epoxidation feed gas (2) include at least a portion of treated recycle gas stream (24) and typically further comprise ethylene, oxygen, ballast gas (e.g., methane or nitrogen), and a reaction modifier (e.g., monochloroethane, vinyl chloride or dichloroethane), which may be supplied to the recycle gas loop via one or more inlets, such as inlet (1).

In epoxidation reactor (4), ethylene is reacted with oxygen in the presence of an epoxidation catalyst to yield epoxidation reaction product stream (6), which typically comprises ethylene oxide, unreacted ethylene and oxygen, reaction modifier, ballast gas, various by-products of the epoxidation reaction (e.g., carbon dioxide and water) and various impurities. Epoxidation reaction product stream (6) exits epoxidation reactor (4) via an outlet, such as outlet (5), which is in fluid communication with an inlet of ethylene oxide absorber (8), such as inlet (7). Preferably, epoxidation reaction product stream (6) is cooled in one or more coolers (not shown), preferably with generation of steam at one or more temperature levels before being supplied to ethylene oxide absorber (8).

Epoxidation reaction product stream (6) and lean absorbent stream (11) are supplied to ethylene oxide absorber (8). In ethylene oxide absorber (8), the epoxidation reaction product is brought into intimate contact with the lean absorbent in the presence of an iodide-containing carboxylation catalyst, and more preferably in the presence of an iodide-containing carboxylation catalyst and a hydrolysis catalyst. At least a portion of, and preferably substantially all of, the ethylene oxide in the epoxidation reaction product is absorbed into the lean absorbent. Fat absorbent stream (9), which comprises ethylene carbonate and/or ethylene glycol, is withdrawn from ethylene oxide absorber (8) via an outlet, such as outlet (10) and may optionally be supplied to one or more finishing reactors (not shown).

Any gases not absorbed in ethylene oxide absorber (8) are withdrawn at or near the top of ethylene oxide absorber (8) as recycle gas stream (13) via an outlet, such as outlet (12), which is in fluid communication with the recycle gas loop. The recycle gas loop comprises interconnecting pipework between outlet (12) of ethylene oxide absorber (8) and inlet (3) of epoxidation reactor (4) and optionally may further comprise heat exchanger(s), a vapor-liquid separator, such as vapor-liquid separator (14) (e.g., knock-out vessel, flash vessel, etc.), a recycle gas compressor, such as recycle gas compressor (16), and/or a carbon dioxide absorber, such as carbon dioxide absorber (26).

Recycle gas stream (13) comprises an alkyl iodide impurity (e.g., methyl iodide and/or ethyl iodide) and a vinyl iodide impurity due to the presence of the iodide-containing carboxylation catalyst in ethylene oxide absorber (8) and the reaction conditions therein. Typically, recycle gas stream (13) further comprises one or more of ethylene, oxygen, reaction modifier, ballast gas, carbon dioxide and water.

To reduce the amount of the iodide impurities, recycle gas stream (13) is supplied to first guard bed system (18) via an inlet, such as inlet (17) that is in fluid communication with the recycle gas loop. In first guard bed system (18), recycle gas stream (13) is brought into contact with a packed bed of a first guard bed material in a guard bed vessel. As mentioned, the first guard bed material comprises a first support material, and deposited on the first support material, silver in an amount of from 2% to 10% by weight. By contacting recycle gas stream (13) with the first guard bed material, at least a portion of the alkyl iodide impurity is removed from recycle gas stream (13) to yield partially treated recycle gas stream (20), which comprises a reduced amount of the alkyl iodide impurity relative to recycle gas stream (13). Partially treated recycle gas stream (20) exits first guard bed system (18) via an outlet, such as outlet (19), which is in fluid communication with second guard bed system (22) via an inlet, such as inlet (21). At least a portion of partially treated recycle gas stream (20) is supplied to second guard bed system (22) wherein it is brought into contact with a packed bed of a second guard bed material in a guard bed vessel. As mentioned, the second guard bed material comprises a second support material, palladium and gold. By contacting partially treated recycle gas stream (20) with the second guard bed material, at least a portion of the vinyl iodide impurity is removed from partially treated recycle gas stream (20) to yield treated recycle gas stream (24), which comprises a reduced amount of the vinyl iodide impurity relative to recycle gas stream (13). Treated recycle gas stream (24) exits second guard bed system (22) via an outlet, such as outlet (23) which is in fluid communication with the recycle gas loop.

Figure 3:
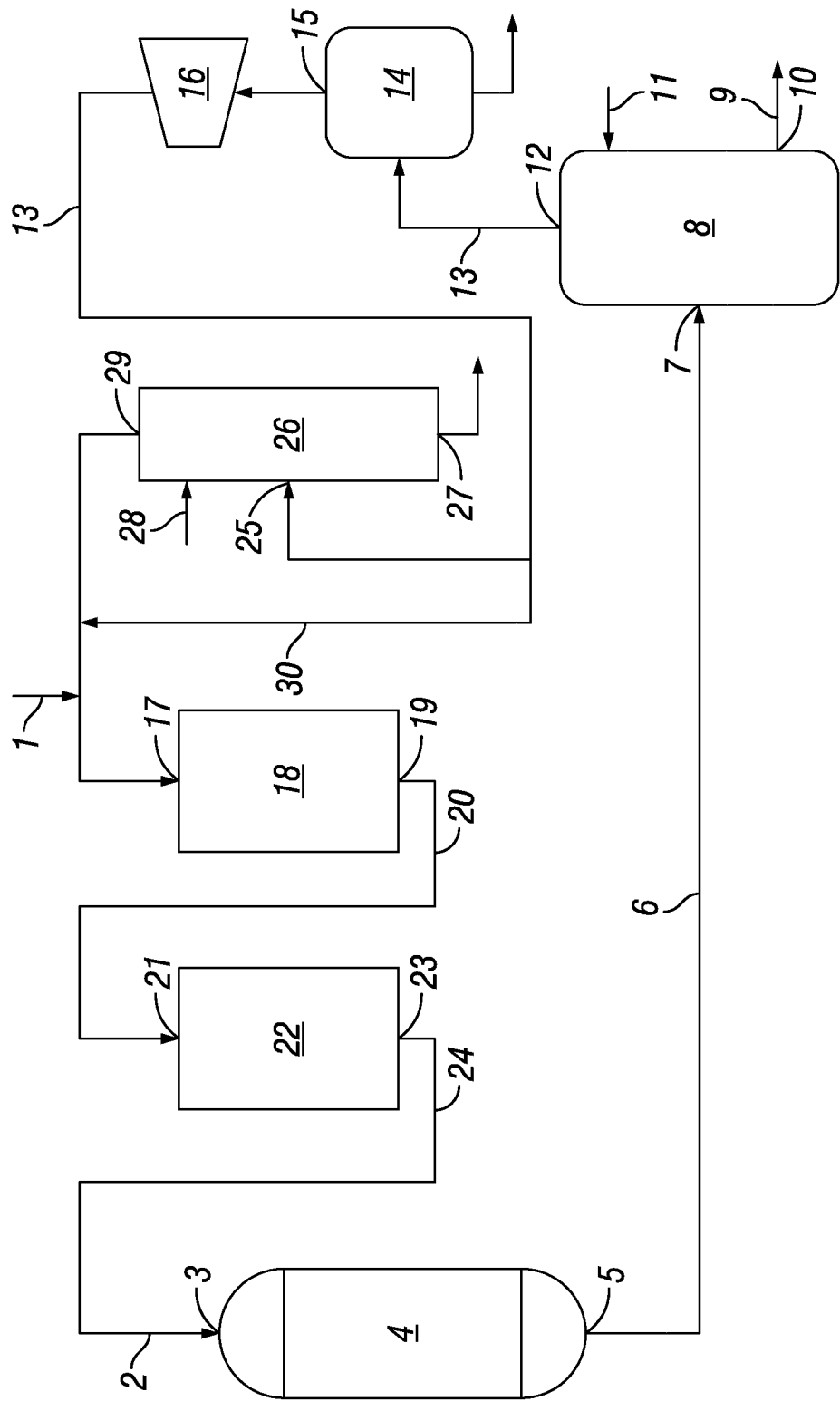

Suitably, first guard bed system (18) and second guard bed system (22) are arranged in series and may be located anywhere in the recycle gas loop. For example, as shown in FIG. 1, first guard bed system (18) and second guard bed system (22) may preferably be located in the recycle gas loop between outlet (12) of ethylene oxide absorber (8) and an inlet of carbon dioxide absorber (26), such as inlet (25), and more preferably between an outlet of recycle gas compressor (16) and inlet (25) of carbon dioxide absorber (26). Also, as shown in FIG. 1, first guard bed system (18) and second guard bed system (22) may preferably be located in the recycle gas loop between an outlet of vapor-liquid separator (14), such as outlet (15), and inlet (3) of epoxidation reactor (4), and more preferably between outlet (15) of vapor-liquid separator (14) and inlet (25) of carbon dioxide absorber (26). Further, as shown in FIG. 1, first guard bed system (18) and second guard bed system (22) may preferably be located in the recycle gas loop upstream from inlet (1), where additional component(s) of epoxidation feed gas (2), such as ethylene, oxygen, ballast gas and/or a reaction modifier, may be supplied to the recycle gas loop, or alternatively, downstream from such a point, as shown in FIG. 3, for example.

Preferably, as shown in FIG. 1, at least a portion of treated recycle gas stream (24) is supplied to carbon dioxide absorber (26) via an inlet, such as inlet (25), along with recirculating absorbent stream (28). In carbon dioxide absorber (26), the treated recycle gas stream is brought into contact with recirculating absorbent stream (28). At least a portion of the carbon dioxide in the treated recycle gas stream is absorbed into the recirculating absorbent stream and is withdrawn from carbon dioxide absorber (26) via an outlet, such as outlet (27). The portion of the treated recycle gas stream that was supplied to carbon dioxide absorber (26), but that was not absorbed by the recirculating absorbent stream exits via an outlet, such as outlet (29), and is preferably re-combined with any portion of the treated recycle gas stream that bypassed carbon dioxide absorber (26) via bypass (30). The treated recycle gas stream is then recycled to inlet (3) of epoxidation reactor (4) as a component of epoxidation feed gas (2).

Optionally, one or more heating or cooling devices, such as a heat exchanger, may be present in the recycle gas loop in order to alter the temperature of recycle gas stream (13) (e.g., so as to provide recycle gas stream (13) to first guard bed system (18) at an optimal temperature), to alter the temperature of partially treated recycle gas stream (20) (e.g., so as to provide partially treated recycle gas stream (20) to second guard bed system (22) at an optimal temperature), and/or in order to alter the temperature of treated recycle gas stream (24) (e.g., so as to provide treated recycle gas stream (24) to epoxidation reactor (4)) or for any further treatment of the treated recycle gas stream prior to being provided to epoxidation reactor (4).

Figure 2:
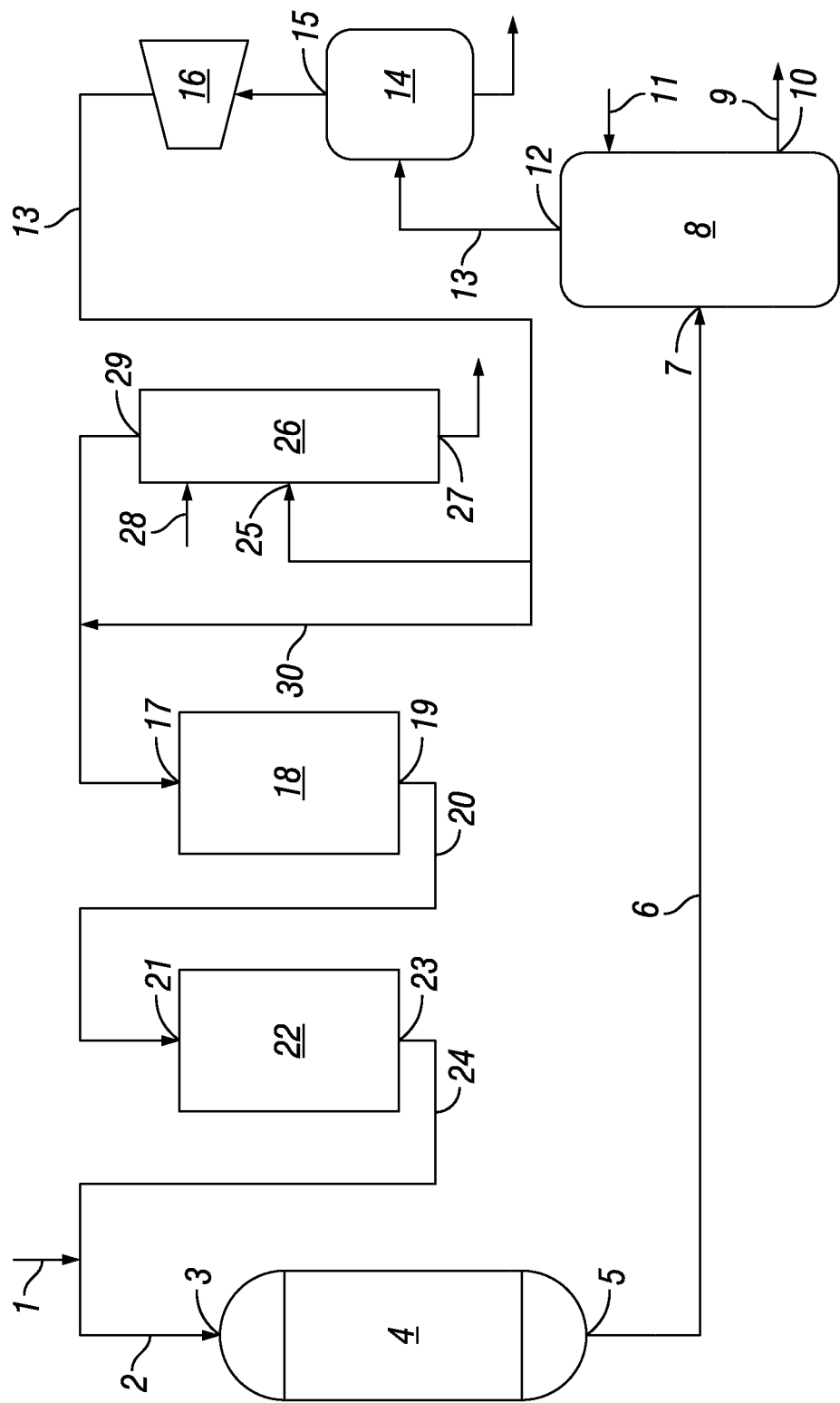

FIG. 2 is a schematic view of a reaction system (31) for the production of ethylene carbonate and/or ethylene glycol, similar to FIG. 1 except that first guard bed system (18) and second guard bed system (22) are positioned in the recycle gas loop downstream from carbon dioxide absorber (26). As shown in FIG. 2, at least a portion of recycle gas stream (13) is supplied to inlet (25) of carbon dioxide absorber (26), while the remaining portion of recycle gas stream (13) (if any) bypasses carbon dioxide absorber (26) via bypass (30). The portion of the recycle gas stream that was supplied to carbon dioxide absorber (26), but that was not absorbed by the recirculating absorbent stream exits via outlet (29), and is preferably re-combined with any portion of the recycle gas stream that bypassed carbon dioxide absorber (26) via bypass (30) and is supplied to inlet (17) of first guard bed system (18). Partially treated recycle gas stream (20) exits first guard bed system (18) via outlet (19) and is supplied to second guard bed system (22) via inlet (21). Treated recycle gas stream (24) exits second guard bed system (22) via outlet (23), which is in fluid communication with the recycle gas loop, and is recycled to inlet (3) of epoxidation reactor (4) as a component of epoxidation feed gas (2).

FIG. 3 is a schematic view of a reaction system (31) for the production of ethylene carbonate and/or ethylene glycol, similar to FIG. 2 except that first guard bed system (18) and second guard bed system (22) are positioned in the recycle gas loop downstream from inlet (1), where one or more additional components of epoxidation feed gas (2), such as ethylene, oxygen, ballast gas and/or a reaction modifier, may be supplied to the recycle gas loop.

Figure 4:
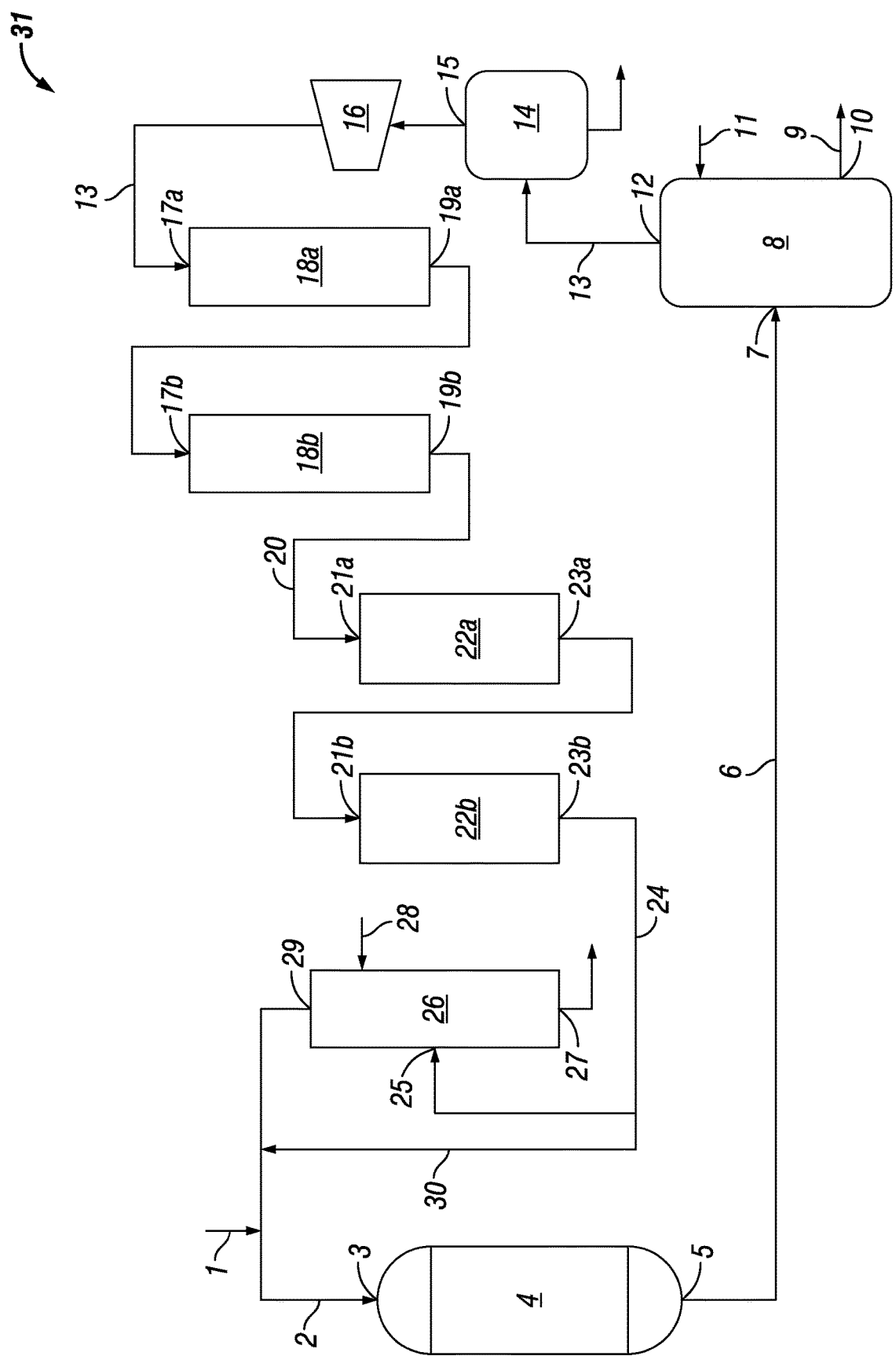

FIG. 4 is a schematic view of a reaction system (31) for the production of ethylene carbonate and/or ethylene glycol, similar to FIG. 1 except that the first and second guard bed systems each comprise a plurality of guard bed vessels. As shown in FIG. 4, recycle gas stream (13) is supplied via inlet (17*a*) to a first guard bed system comprising two guard bed vessels (18*a*) and (18*b*) that each comprise a packed bed of a first guard bed material. The gas stream exiting guard bed vessel (18*a*) via outlet (19*a*) is subsequently supplied to guard bed vessel (18*b*) via inlet (17*b*). Partially treated recycle gas stream (20) exits the first guard bed system via outlet (19*b*) and is supplied via inlet (21*a*) to a second guard bed system comprising two guard bed vessels (22*a*) and (22*b*) that each comprise a packed bed of a second guard bed material. The gas stream exiting guard bed vessel (22*a*) via outlet (23*a*) is subsequently supplied to guard bed vessel (22*b*) via inlet (21*b*). Treated recycle gas stream (24) exits the second guard bed system via outlet (23*b*), which is in fluid communication with the recycle gas loop. Preferably, at least a portion of treated recycle gas stream (24) is supplied to carbon dioxide absorber (26) before it is recycled to inlet (3) of epoxidation reactor (4) as a component of epoxidation feed gas (2).

As mentioned, reaction systems of the present disclosure comprise two or more guard bed systems arranged in series (e.g., a first guard bed system, a second guard bed system, etc.), with each guard bed system comprising an inlet, an outlet, and one or more guard bed vessels that each comprise a bed of guard bed material. Suitably, an inlet of a first guard bed system is fluidly connected to the recycle gas loop so that at least a portion of a recycle gas stream from the ethylene oxide absorber is supplied (either directly or indirectly) to the first guard bed system. Within the first guard bed system, the recycle gas stream passes through the one or more guard bed vessels and contacts a first guard bed material whereby alkyl iodide impurities are removed. A partially treated recycle gas stream is removed from an outlet of the first guard bed system and supplied to an inlet of a second guard bed system. Within the second guard bed system, the partially treated recycle gas stream passes through the one or more guard bed vessels and contacts a second guard bed material whereby vinyl iodide is removed. A treated recycle gas stream is removed from an outlet of the second guard bed system. Said treated recycle gas stream will contain a reduced amount of alkyl iodide and vinyl iodide impurities as compared to the recycle gas stream. Suitably, the outlet of the second guard bed system is fluidly connected to the recycle gas loop so that at least a portion of a treated recycle gas stream from the second guard bed system is supplied (either directly or indirectly) to an inlet of the epoxidation reactor.

Each guard bed system preferably comprises two or more guard bed vessels. Optionally, each guard bed system comprises more than two, for example three or four, guard bed vessels. The number of guard bed vessels contained within each guard bed system may be the same or different. Within a given guard bed system, the guard bed vessels may be arranged in parallel with associated switching means to allow the process to be switched between the vessels, thus maintaining a continuous operation of the process. Alternatively, the guard bed vessels within a guard bed system may be arranged in series or in series in sequential order, with associated valves, as described in co-pending application EP15200254.9, which is incorporated by reference herein.

Guard bed vessels suitable for use in the present disclosure include any vessel in which a bed of guard bed material can be held and through which a gas stream can be passed such that the gas stream comes into contact with the guard bed material. Preferably, a guard bed vessel is a fixed bed reactor, such as an axial fixed bed reactor, wherein the gas stream is contacted with a guard bed material as an axial flow; or a radial flow fixed bed reactor, wherein the gas stream is supplied from an inlet to the outside of the fixed bed and passes through the fixed bed to the center of the guard bed vessel and then to an outlet. A radial flow fixed bed reactor is particularly preferred because it will generally produce less of a pressure drop across the bed of guard bed material. Other suitable types of guard bed vessels will be apparent to those of ordinary skill in the art and are to be considered within the scope of the present disclosure.

Without wishing to be bound by any particular theory, it is believed that by contacting a gas stream comprising an alkyl iodide impurity and/or a vinyl iodide impurity with a first and/or second guard bed material of the present disclosure, at least a portion of the alkyl iodide impurity and/or vinyl iodide impurity present in the gas stream is removed by chemical or physical means including, but not limited to, reaction with the impurity and absorption of the impurity.

The operating conditions within the one or more guard bed vessels in a given guard bed system can be adjusted according to overall processing conditions. Further, the operating conditions in each guard bed system may be the same or different, depending on, for example, the guard bed material contained therein or the type of impurity that should be removed. In general, the pressure in the one or more guard bed vessels in a guard bed system is determined by the pressure of the recycle gas loop. Preferably, the operating pressure can range from 1 to 4 MPa (gauge), more preferably from 2 to 3 MPa (gauge). Additionally, a guard bed vessel in a guard bed system is generally operated at an elevated temperature (relative to ambient).

Preferably, the one or more guard bed vessels in a first guard bed system are operated at a temperature of at least 80° C., more preferably at least 100° C., even more preferably at least at least 115° C., most preferably at least 120° C. Further, the one or more guard bed vessels in a first guard bed system are preferably operated at a temperature of at most 145° C., more preferably at most 140° C., most preferably at most 135° C., or from 100° C. to 145° C., or from 115° C. to 140° C., or from 120° C. to 135° C.

Preferably, the one or more guard bed vessels in a second guard bed system are operated at a temperature of at least 65° C., more preferably at least 70° C., most preferably at least 83° C. Further, the one or more guard bed vessels in a second guard bed system are preferably operated at a temperature of at most 95° C., more preferably at most 90° C., most preferably at most 87° C., or from 65° C. to 95° C., or from 70° C. to 90° C., or from 83° C. to 87° C.

Each guard bed vessel comprises a bed of guard bed material. It is preferred that all guard bed vessels within a single guard bed system contain the same guard bed material. Suitable bed dimensions of a bed of guard bed material may readily be determined using known engineering principles. Preferably, a guard bed vessel comprises a guard bed material present in a bed that is sized to provide a contact time of the guard bed material with the incoming gas stream that is sufficient to provide the desired degree of removal of the alkyl iodide and/or vinyl iodide impurity from the gas stream.

In accordance with the present disclosure, one or more guard bed vessels in a first guard bed system comprise a first guard bed material that comprises a first support material, and deposited on the first support material, silver in an amount of from 2% to 10% by weight. Suitably, the first support material may comprise alumina, titania, zirconia, silica, activated carbon, or any combination thereof. Preferably, the first support material comprises alumina, in particular gamma-alumina. A suitable first support material may have a surface area of more than 20 $m^2/g$, relative to the weight of the support material, or at least 25 $m^2/g$, or at least 50 $m^2/g$, or at least 75 $m^2/g$, or at least 100 $m^2/g$, or at least 125 $m^2/g$, or at most 1200 $m^2/g$, or at most 500 $m^2/g$, or at most 300 $m^2/g$, or at most 200 $m^2/g$, or at most 175 $m^2/g$, or from 20 $m^2/g$ to 1200 $m^2/g$, or from 50 $m^2/g$ to 500 $m^2/g$, or from 75 $m^2/g$ to 300 $m^2/g$, or from 100 $m^2/g$ to 200 $m^2/g$, or from 125 $m^2/g$ to 175 $m^2/g$, on the same basis. As used herein, "surface area" is understood to refer to the surface area of the support material as measured in accordance with the B.E.T. (Brunauer, Emmett and Teller) method as described in detail in Brunauer, S., Emmet, P. Y. and Teller, E., J. Am. Chem. Soc., 60, pgs. 309-316 (1938).

Suitable shapes for a first support material include any of the wide variety of shapes known for such materials, which include, but are not limited to, particles, pills, chunks, tablets, pieces, pellets, rings, spheres, wagon wheels, trapezoidal bodies, doughnuts, amphora, rings, Raschig rings, honeycombs, monoliths, saddles, cylinders, hollow cylinders, multi-lobed cylinders, cross-partitioned hollow cylinders (e.g., cylinders having at least one partition extending between walls), cylinders having gas channels from side wall to side wall, cylinders having two or more gas channels, and ribbed or finned structures. While the cylinders are often circular, other cross-sections, such as oval, hexagonal, quadrilateral, trilateral, and multi-lobed may be useful. Preferably, the first support material is spherical. As used herein, the term "spherical" refers to a support material that, when observed under a scanning electron microscope, has a major axis to minor axis ratio of 1.0 to 1.25. Preferably, the first support material is a spherical support material and has a diameter of less than 2 mm, or 1.8 mm or less, or 1.6 mm or less, or 1.5 mm or less, or 1.3 mm or less, or 1.0 mm or less, or a diameter from 0.25 mm to less than 2 mm, or from 0.5 mm to less than 2 mm, or from 0.75 mm to less than 2 mm, or from 1 mm to less than 2 mm, or from 0.25 mm to 1.5 mm, or from 0.5 mm to 1.5 mm, or from 0.75 mm to 1.5 mm, or from 1 mm to 1.5 mm.

The first guard bed material further comprises silver, which is deposited on the first support material, in an amount of at least 2% by weight and no more than 10% by weight, calculated as the amount of silver relative to the total weight of the first guard bed material. Preferably, the first guard bed material comprises silver in an amount of from 2% to 10% by weight, or from 2% to 9% by weight, or from 2% to 8% by weight, or from 2% to 7% by weight, or from 2% to 6% by weight, or from 3% to 9%, or from 3% to 8%, or from 3% to 7%, or from 3% to 6%, or from 4% to 8% by weight, or from 4.5% to 7% by weight, or at most 8% by weight, or at most 7% by weight, or at most 6% by weight, on the same basis. Although it is possible for a first guard bed material to comprise silver in an amount in excess of 10% by weight, it is preferred to employ silver in an amount of 10% by weight or less, as little to no benefit is derived from the further addition of silver.

Optionally, the first guard bed material further comprises at least one of an alkali metal, an alkaline earth metal, or a combination thereof. Preferably, the alkali metal may be selected from sodium, potassium, lithium, rubidium, cesium, and combinations thereof, in particular sodium and potassium. Preferably, the alkaline earth metal may be selected from calcium, magnesium, strontium, barium, and combinations thereof. The specific form in which an alkali and/or alkaline earth metal is provided is not limited, and may include any of the wide variety of forms known. For example, the alkali and/or alkaline earth metal may suitably be provided as an ion (e.g., cation), or as a compound (e.g., alkali metal salts, alkaline earth metal salts, etc.). Generally, suitable compounds are those which can be solubilized in an appropriate solvent, such as a water-containing solvent. Without wishing to be bound by theory, it is believed that the alkali or alkaline earth metals reduce the amount of acidic sites present on the surface of the support material which can react with a hydrocarbon, such as ethylene, forming unwanted by-products.

As will be appreciated by those of skill in the art, while a specific form of an alkali and/or alkaline earth metal may be provided during preparation of the first guard bed material, it is possible that during the conditions of preparation of the first guard bed material and/or during use, the particular form initially present may be converted to another form. Indeed, once deposited on the support material and/or during use of the first guard bed material, the specific form of the alkali and/or alkaline earth metal may not be known. Furthermore, in many instances, analytical techniques may not be sufficient to precisely identify the form that is present. Accordingly, the present disclosure is not intended to be limited by the exact form of the alkali and/or alkaline earth metal that may ultimately exist on the first guard bed material during use. Additionally, it should be understood that while a particular compound may be used during preparation (e.g., potassium hydroxide is added to an impregnation solution), it is possible that the counter ion added during preparation of the first guard bed material may not be present in the finished first guard bed material (e.g., a first guard bed material made using an impregnation solution comprising potassium hydroxide may be analyzed to contain potassium but not hydroxide in the finished first guard bed material).

When included, an alkali metal, an alkaline earth metal or a combination thereof may be deposited on the first support material in an amount of at least 0.1% by weight and no more than 5% by weight, calculated as the amount of the element relative to the total weight of the first guard bed material. Preferably, the first guard bed material comprises an alkali metal, an alkaline earth metal or a combination thereof in an amount of from 0.1% to 5% by weight, or from 0.2% to 4% by weight, or from 0.3% to 3% by weight, or from 0.4% to 2% by weight, or from 0.5% to 1% by weight or at least 0.1% by weight, or at least 0.2% by weight, or at least 0.3% by weight, or at least 0.4% by weight, or at least 0.5% by weight, or at most 5%, or at most 4%, or at most 3%, or at most 2%, on the same basis. For purposes of convenience, the amount of the alkali or alkaline earth metal deposited on a first support material is measured as the element, irrespective of the form in which it is present. Although it is possible for a first guard bed material to comprise an alkali metal, an alkaline earth metal or a combination thereof in an amount in excess of 5% by weight, it is preferred to employ an alkali metal, an alkaline earth metal or a combination thereof in an amount of 5% by weight or less, as little to no benefit is derived from the further addition of an alkali metal, an alkaline earth metal or a combination thereof.

It should be understood that the amount of alkali and/or alkaline earth metal deposited on the first support material is not necessarily the total amount of alkali and/or alkaline earth metal present in the first guard bed material. Rather, the amount deposited reflects the amount that has been added to the support material (e.g., via impregnation). As such, the amount of alkali and/or alkaline earth metal deposited on the support material does not include any amount of alkali and/or alkaline earth metals that may be locked into the support material, for example, by calcining, or are not extractable in a suitable solvent, such as water or lower alkanol or amine or mixtures thereof. It is also understood that the source of the alkali and/or alkaline earth metal may be the support material itself. That is, the support material may contain extractable amounts of an alkali and/or alkaline earth metal that can be extracted with a suitable solvent, such as water or lower alkanol, thus preparing a solution from which the alkali and/or alkaline earth metal may be deposited or redeposited on the support material.

Well known methods can be employed to analyze for the amounts of silver, and alkali and/or alkaline earth metal deposited onto the support material. The skilled artisan may employ, for example, material balances to determine the amounts of any of these deposited components. As an example, if the support material is weighed prior to and after deposition of silver and an alkali or alkaline earth metal, then the difference in the two weights will be equal to the amount of silver and the alkali or alkaline earth metal deposited onto the support material, from which the amount of the deposited alkali and/or alkaline earth metal can be calculated. Additionally, the amount of the deposited silver and alkali and/or alkaline earth metal can be calculated based upon the ratio of the concentration of silver and alkali or alkaline earth metal included in the impregnation solution(s) and the total weight in the finished first guard bed material.

Alternatively, the amount of an alkali and/or alkaline earth metal deposited on the support material may also be determined by known leaching methods, wherein the amount of metallic leachables present in the support material and the amount of metallic leachables present in the first guard bed material are independently determined and the difference between the two measurements reflect the total amount of alkali or alkaline earth metal deposited on the support material. As an example, the amount of an alkali metal deposited on a support material may be determined by separately leaching a 10-gram sample of the support material and a 10-gram sample of the first guard bed material with 100 mL of 10% w nitric acid for 30 minutes at 100° C. (1 atm) and determining the amount of the alkali metal present in the extracts using standard Atomic Absorption spectroscopy techniques. The difference in the measurements between the support material and the first guard bed material reflect the amount of the alkali metal deposited onto the support material.

The specific manner in which a first guard bed material is prepared is generally not limited, and therefore any known preparative method may be used, provided that the silver and optionally, the alkali and/or alkaline earth metal are deposited on the support material in a suitable manner. In general, a first guard bed material may be prepared by contacting (e.g., impregnating) a first support material with one or more solutions comprising silver and optionally, at least one of an alkali metal, an alkaline earth metal, or a combination thereof; and subsequently depositing silver and the alkali and/or alkaline metal (if present) on the support material, typically by heating the impregnated support material. For further description of impregnation methods, reference may be made to U.S. Pat. Nos. 4,761,394, 4,766,105, 5,380,697, 5,739,075, 6,368,998 and 6,656,874, which are incorporated herein by reference. Furthermore, for additional disclosure regarding suitable first guard bed materials, reference may be made to co-pending application EP15200267.1, which is incorporated by reference herein.

In a second guard bed system, the one or more guard bed vessels comprise a second guard bed material that comprises a second support material, palladium (Pd) and gold (Au). With respect to suitable second support materials, such support materials are generally known in the art. The specific support material used in the second guard bed material is not particularly limited and therefore any of the conventional support materials heretofore used for the preparation of palladium-gold catalysts, which are typically used in the production of vinyl acetate by the vapor phase reaction of ethylene, acetic acid and oxygen, can be used. Illustrative of such support materials are those comprising silica, alumina, silica-alumina, silica gel, silicic acid, silicates, silicon carbide, titania, zirconia, tungsten trioxide, pumice, magnesia, zeolites, and combinations thereof. Preferably, the second support material comprises silica, and may or may not further comprise alumina. In these embodiments, the silica content of the second support material may be at least 50 wt. %, more typically at least 90 wt. %, based on the weight of the support material. Frequently, the silica content of the second support material is at most 99.99 wt. %, more frequently at most 99.9 wt. %, on the same basis.

Suitable shapes for a second support material include any of the wide variety of shapes known for such materials, which include, but are not limited to, particles, pills, chunks, tablets, pieces, pellets, rings, spheres, wagon wheels, trapezoidal bodies, doughnuts, amphora, rings, Raschig rings, honeycombs, monoliths, saddles, cylinders, hollow cylinders, multi-lobed cylinders, cross-partitioned hollow cylinders (e.g., cylinders having at least one partition extending between walls), cylinders having gas channels from side wall to side wall, cylinders having two or more gas channels, and ribbed or finned structures. While the cylinders are often circular, other cross-sections, such as oval, hexagonal, quadrilateral, trilateral, and multi-lobed may be useful. Additionally, the size of the second support material is generally not limited, and may include any size suitable for use in a guard bed vessel. Preferably, the second support material is in the form of particles or spheres having a diameter of from about 2 to 10 mm, or from 3 to 9 mm, or from 4 to 7 mm.

Suitable second guard bed material further comprises palladium in an amount of at least 0.1% by weight and no more than 3% by weight, calculated as the amount of palladium relative to the total weight of the second guard bed material. Preferably, the second guard bed material comprises palladium in an amount of from 0.1% to 3% by weight, or from 0.5% to 2.5% by weight, or from 0.5% to 2.2% by weight, or from 0.8% to 2.2% by weight, or from 1% to 2% by weight, or at most 3% by weight, or at most 2.5% by weight, or at most 2.2% by weight, or at most 2% by weight, on the same basis. As used herein, unless otherwise specified, the total weight of the second guard bed material is understood to refer to the weight of the support material and all components deposited thereon, including palladium and gold.

In addition to palladium, the second guard bed material further comprises gold in an amount of at least 0.1% by weight and no more than 3% by weight, calculated as the amount of gold relative to the total weight of the second guard bed material. Preferably, the second guard bed material comprises gold in an amount of from 0.1% to 3% by weight, or from 0.1% to 2.5% by weight, or from 0.5% to 2% by weight, or from 0.5% to 1.5% by weight, or from 0.7% to 1.2% by weight, or from 0.5% to 1% by weight, or from 0.7% to 1% by weight, or at most 3% by weight, or at most 2.5% by weight, or at most 2% by weight, or at most 1.5% by weight, or at most 1% by weight, on the same basis. One example of a suitable second guard bed material is KL7905, which is a spherical material comprising palladium and gold on a silica support commercially available from CRI Catalyst.

The specific manner in which a second guard bed material is prepared is not limited, and therefore any known preparative method may be used, provided that the palladium and gold are provided on the support material in a suitable manner. In general, a second guard bed material may be prepared by impregnating a second support material with one or more aqueous impregnation solutions comprising palladium and gold. Further, an impregnated support material may optionally be contacted with a precipitating agent to precipitate palladium and/or gold from such impregnating solution(s) and/or contacted with a reducing agent to convert the palladium and/or gold into metallic species. As used herein, the phrase "impregnating a support material with one or more aqueous impregnation solutions comprising palladium and gold" and similar or cognate terminology means that the second support material is impregnated in a single or multiple step with one aqueous impregnation solution comprising palladium and gold; or in multiple steps with two or more aqueous impregnation solutions, wherein each aqueous impregnation solution comprises at least one component selected from palladium and gold, with the proviso that palladium and gold will individually be found in at least one of the aqueous impregnation solutions. Furthermore, as is known in the art, the sequence of contacting the support material with one or more aqueous impregnation solutions comprising palladium and gold may vary. Thus, impregnation of palladium and gold may be effected coincidentally or sequentially. In more detail, the applicable materials and methods may include those as disclosed in U.S. Pat. Nos. 4,048,096, 5,179,057, 5,189,004, 7,425,647, WO 1999008790 and WO 1999008791, which are incorporated herein by reference. Furthermore, for additional disclosure regarding suitable second guard bed materials, reference may be made to co-pending application EP 15200272.1, which is incorporated by reference herein.

Optionally, a second support material be washed and/or treated prior to or subsequent impregnation. Any method known in the art for washing and/or treating may be used in accordance with the present disclosure, provided that such method does not negatively affect the performance of the second guard bed material. Reference is made to U.S. Pat. Nos. 7,030,056 and 7,425,647 which are incorporated herein by reference.

Although second guard bed materials suitable for use herein are typically prepared by impregnating a second support material with one or more aqueous solutions (commonly referred to as "aqueous impregnation solution(s)") comprising palladium and gold, the present disclosure is not intended to be limited to any particular preparation method. Accordingly, any known preparative method may be used provided that palladium, gold, and any other optional components (if any) are provided on the second support material in a suitable manner.

Following impregnation of the second support material with the one or more aqueous impregnation solutions, the second support material optionally may be contacted with a precipitating agent. A suitable precipitating agent may include, for example, alkali metal silicates, alkali metal hydroxides, alkali metal bicarbonates, alkali metal carbonates and combinations thereof. Suitable alkali metals are lithium, sodium, potassium and combinations thereof. Preferably, the precipitating agent is sodium silicate, such as sodium metasilicate and hydrated sodium metasilicate. Suitable precipitating agents and precipitation methods are known from U.S. Pat. Nos. 4,048,096, 5,179,057, 5,189,004, 7,030,056, and 7,425,647, which are incorporated herein by reference.

Optionally, following impregnation of the second support material with the one or more aqueous impregnation solutions or after precipitation, the support may be contacted with a reducing agent. A suitable reducing agent may include, for example, diborane; amines, such as ammonia and hydrazine; carboxylic acids and their salts, such as oxalic acid, potassium oxalate, formic acid, potassium formate, ammonium citrate; aldehydes, such as formaldehyde, acetaldehyde; hydrogen peroxide; reducing sugars such as glucose; alcohols other than reducing sugars, such as methanol and ethanol; polyhydric phenols, such as hydroquinone and catechol; hydrogen; carbon monoxide; olefins, such as ethylene, propene and isobutene; sodium borohydride; and combinations thereof. Suitable reducing agents and reduction methods are known from U.S. Pat. Nos. 4,048,096, 5,179,057, 5,189,004, 7,030,056, and 7,425,647, which are incorporated herein by reference.

In another embodiment, palladium and gold are precipitated and reduced to metallic species in one step, following, for example, procedures as disclosed in WO 1999008790 and WO 1999008791, which are herein incorporated by reference.

Optionally, second guard bed materials suitable for use herein may further comprise an alkali metal. Typically, such a second guard bed material may be prepared by impregnating a second support material (or the second guard bed material comprising palladium and gold) with a source of an alkali metal, such as those disclosed in U.S. Pat. Nos. 4,048,096, 5,179,057 and 5,189,004, which are herein incorporated by reference. Suitable sources of an alkali metal include, for example, alkali metal carbonates and alkali metal carboxylates. The alkali metal carboxylate is typically derived from a mono carboxylic acid, such as butyric acid, propionic acid and, preferably, acetic acid. The alkali metal may be any one or more of lithium, sodium, potassium, rubidium and cesium. Preferably, the alkali metal is potassium. The preferred alkali metal carboxylate is potassium acetate. The quantity of the alkali metal carboxylate is typically such that the alkali metal content of the second guard bed material is in the range of from 0.1 to 5 mole/kg, more preferably from 0.2 to 2 mole/kg, for example 340 mmole/kg, or 585 mmole/kg, or 765 mmole/kg, or 1560 mmole/kg.

Optionally, at certain stages of the second guard bed material preparation it may be desirable to perform a drying step. Drying is typically performed at a temperature in the range of from 50 to 300° C., more typically in the range of from 80 to 150° C., for example 90° C., or 115° C., or 120° C., using an inert gas, such as nitrogen or helium, or air.

Processes of the present disclosure further comprise contacting an epoxidation feed gas comprising ethylene, oxygen and at least a portion of the treated recycle gas stream with an epoxidation catalyst to yield an epoxidation reaction product comprising ethylene oxide. Although an epoxidation process may be carried out in a variety of known ways, it is preferred to carry out the epoxidation process as a continuous, gas-phase process, wherein an epoxidation feed gas is contacted with an epoxidation catalyst in the gas phase in an epoxidation reactor. The following description provides further details of the epoxidation catalyst, epoxidation reactor, epoxidation feed gas and the epoxidation process.

Suitable epoxidation catalysts that may be employed are known in the art and generally comprise a carrier, and deposited on the carrier, silver and optionally, one or more promoters, such a rhenium promoter, an alkali metal promoter, etc. Detailed preparative techniques for carriers and epoxidation catalysts are generally known in the art. For additional disclosure regarding suitable epoxidation catalysts and preparative techniques, reference may be made to, for example U.S. Pat. Nos. 4,761,394, 8,921,586 and 8,932,979 and U.S. Patent Publication Nos. 20080281118 and 20110034710, which are incorporated herein by reference.

An epoxidation reactor suitable for use in the systems and processes of the present disclosure may be any reactor vessel used to react ethylene and oxygen in the presence of an epoxidation catalyst, and comprises an inlet that is in fluid communication to the recycle gas loop and further comprises an outlet that is in fluid communication with an inlet of an ethylene oxide absorber. Suitable epoxidation reactors may include any of a wide variety of known reactor vessels, such as a fixed bed reactor (e.g., a fixed bed tubular reactor), a continuous stirred tank reactor (CSTR), a fluid bed reactor, etc. Additionally, a plurality of epoxidation reactors may be used in parallel. One commercial example of a suitable epoxidation reactor is a shell-and-tube heat exchanger comprising a plurality of reactor tubes, wherein the shell contains a coolant to regulate the temperature of the epoxidation reactor and wherein the plurality of tubes are parallel, elongated tubes that contain the epoxidation catalyst.

In accordance with the present disclosure, an epoxidation feed gas comprises ethylene, oxygen and a treated recycle gas stream. Optionally, the epoxidation feed gas may further comprise carbon dioxide, a ballast gas, a reaction modifier, and a combination thereof. As used herein, the term "epoxidation feed gas" refers to the totality of the gas stream supplied at the inlet of the epoxidation reactor, which may suitably be comprised of a combination of one or more gas stream(s), such as an ethylene stream, an oxygen stream, a treated recycle gas stream, etc. Further, it should be understood that the concentrations discussed below of individual feed components in the epoxidation feed gas reflect the total concentration of that component in the epoxidation feed gas, irrespective of the source(s).

Ethylene may be present in the epoxidation feed gas in a concentration that may vary over a wide range. However, ethylene is typically present in the epoxidation feed gas in a concentration of at least 5 mole-%, relative to the total epoxidation feed gas, or at least 8 mole-%, or at least 10 mole-%, or at least 12 mole-%, or at least 14 mole-%, or at least 20 mole-%, or at least 25 mole-%, on the same basis. Similarly, ethylene is typically present in the epoxidation feed gas in a concentration of at most 65 mole-%, or at most 60 mole-%, or at most 55 mole-%, or at most 50 mole-%, or at most 48 mole-%, on the same basis. In some embodiments, ethylene may be present in the epoxidation feed gas in a concentration of from 5 mole-% to 60 mole-%, relative to the total epoxidation feed gas, or from 10 mole-% to 50 mole-%, or from 12 mole-% to 48 mole-%, on the same basis.

In addition to ethylene, the epoxidation feed gas further comprises oxygen, which may be provided either as pure oxygen or air. See W. E. Evans, J. M. Kobe, M. F. Lemanski and R. L. June, "Industrial Epoxidation Processes", Encyclopedia of Catalysis (Wiley-Interscience), Volume 3, page 246 (2003). In an air-based process, air or air enriched with oxygen is employed, while in an oxygen-based process, high-purity (at least 95 mole-%) oxygen or very high purity (at least 99.5 mole-%) oxygen is employed. Reference may be made to U.S. Pat. No. 6,040,467, incorporated by reference herein, for further description of oxygen-based epoxidation processes. Presently, most epoxidation plants are oxygen-based, which is preferred. Typically, in oxygen-based processes, the epoxidation feed gas further comprises a ballast gas, which will be discussed in more detail below, to maintain the oxygen concentration below the maximum level allowed by flammability considerations.

In general, the oxygen concentration in the epoxidation feed gas should be less than the concentration of oxygen that would form a flammable mixture at either the inlet or the outlet of the epoxidation reactor at the prevailing operating conditions. Often, in practice, the oxygen concentration in the epoxidation feed gas may be no greater than a predefined percentage (e.g., 95%, 90%, etc.) of oxygen that would form a flammable mixture at either the inlet or the outlet of the epoxidation reactor at the prevailing operating conditions. Although the oxygen concentration may vary over a wide range, the oxygen concentration in the epoxidation feed gas is typically at least 0.5 mole-%, relative to the total epoxidation feed gas, or at least 1 mole-%, or at least 2 mole-%, or at least 3 mole-%, or at least 4 mole-%, or at least 5 mole-%, on the same basis. Similarly, the oxygen concentration of the epoxidation feed gas is typically at most 20 mole-%, relative to the total epoxidation feed gas, or at most 15 mole-%, or at most 12 mole-%, or at most 10 mole-%, on the same basis. In some embodiments, oxygen may be present in the epoxidation feed gas in a concentration of from 1 mole-% to 15 mole-%, relative to the total epoxidation feed gas, or from 2 mole-% to 12 mole-%, or from 3 mole-% to 10 mole-%, on the same basis. Typically, as the oxygen concentration in the epoxidation feed gas increases, the required operating temperature decreases. However as previously mentioned, in practice, flammability is generally the limiting factor for the maximum concentration of oxygen in the epoxidation feed gas. Accordingly, in order to remain outside the flammable regime, the oxygen concentration of the epoxidation feed gas may be lowered as the ethylene concentration of the epoxidation feed gas is increased. It is within the ability of one skilled in the art to determine a suitable concentration of oxygen to be included in the epoxidation feed gas, taking into consideration, for example, the overall epoxidation feed gas composition, along with the other operating conditions, such as pressure and temperature.

Optionally, the epoxidation feed gas may further comprise carbon dioxide. When present, carbon dioxide is typically present in the epoxidation feed gas in a concentration of 0.10 mole-% or greater, relative to the total epoxidation feed gas, or 0.12 mole-% or greater, or 0.15 mole-% or greater, or 0.17 mole-% or greater, or 0.20 mole-% or greater, or 0.22 mole-% or greater, or 0.25 mole-% or greater, on the same basis. Similarly, carbon dioxide is generally present in the epoxidation feed gas in a concentration of at most 10 mole-%, relative to the total epoxidation feed gas, or at most 8 mole-%, or at most 5 mole-%, or at most 3 mole-%, or at most 2.5 mole-%, on the same basis. In some embodiments, carbon dioxide may be present in the epoxidation feed gas in a concentration of from 0.10 mole-% to 10 mole-%, relative to the total epoxidation feed gas, or from 0.15 mole-% to 5 mole-%, or from 0.20 mole-% to 3 mole-%, or from 0.25 mole-% to 2.5 mole-%, on the same basis. Carbon dioxide is produced as a by-product of the epoxidation reaction and is typically introduced into the epoxidation feed gas as a component of the treated recycle gas stream. Carbon dioxide generally has an adverse effect on catalyst performance, with the operating temperature increasing as the concentration of carbon dioxide present in the epoxidation feed gas increases. Accordingly, in the commercial production of ethylene oxide, it is common for at least a portion of the carbon dioxide to be continuously removed (e.g., via a carbon dioxide absorber) to maintain the concentration of carbon dioxide in the epoxidation feed gas at an acceptable level.

The epoxidation feed gas optionally may further comprise a ballast gas, such as nitrogen, methane, or a combination thereof. When used, a ballast gas may be added to the epoxidation feed gas to increase the oxygen flammability concentration. If desired, a ballast gas may be present in the epoxidation feed gas in a concentration of at least 5 mole-%, relative to the total epoxidation feed gas, or at least 10 mole-%, or at least 20 mole-%, or at least 25 mole-%, or at least 30 mole-%, on the same basis. Similarly, a ballast gas may be present in the epoxidation feed gas in a concentration of at most 80 mole-%, relative to the total epoxidation feed gas, or at most 75 mole-%, or at most 70 mole-%, or at most 65 mole-%, on the same basis. In some embodiments, a ballast gas may be present in the epoxidation feed gas in a concentration of from 20 mole-% to 80 mole-%, relative to the total epoxidation feed gas, or from 30 mole-% to 70 mole-%, on the same basis.

Optionally, the epoxidation feed gas may further comprise a reaction modifier. If desired, a reaction modifier may be added to the epoxidation feed gas to increase the selectivity of the epoxidation catalyst. Examples of suitable reaction modifiers may include, but are not limited to, organic chlorides (e.g., $C_1$ to $C_3$ chloro hydrocarbons). Specific examples of suitable organic chlorides include, but are not limited to, methyl chloride, ethyl chloride, ethylene dichloride, vinyl chloride, and a combination thereof.

A reaction modifier may optionally be present in the epoxidation feed gas in a concentration of 0.1 parts per million by volume (ppmv) or greater, relative to the total epoxidation feed gas, or 0.3 ppmv or greater, or 0.5 ppmv or greater, on the same basis. Similarly, a reaction modifier is generally present in the epoxidation feed gas in a concentration of at most 25 ppmv, relative to the total epoxidation feed gas, or at most 22 ppmv, or at most 20 ppmv, on the same basis. In some embodiments, a reaction modifier may be present in the epoxidation feed gas in a concentration of from 0.1 to 25 ppmv, relative to the total epoxidation feed gas, or from 0.3 to 20 ppmv, on the same basis. Typically, as the epoxidation feed gas composition changes and/or as one or more of the operating conditions change, the concentration of reaction modifier in the epoxidation feed gas may also be adjusted so as to maintain the optimum concentration. For additional disclosure regarding reaction modifiers and optimum concentrations thereof, reference may be made to, for example U.S. Pat. Nos. 7,193,094 and 8,546,592, which are incorporated herein by reference.

Optionally, the epoxidation feed gas may be substantially free, and preferably completely free, of a nitrogen-containing reaction modifier. That is to say, the epoxidation feed gas may comprise less than 100 ppm of a nitrogen-containing reaction modifier, preferably less than 10 ppm, more preferably less than 1 ppm, and most preferably 0 ppm of a nitrogen-containing reaction modifier. As used herein, the term "nitrogen-containing reaction modifier" refers to a gaseous compound or volatile liquid that is present as, or capable of forming, nitrogen oxides in oxidizing conditions. Examples of nitrogen-containing reaction modifiers include, but are not limited to, NO, $NO_2$, $N_2O_3$, $N_2O_4$, $N_2O_5$ or any substance capable of forming one of the aforementioned gases under epoxidation conditions (e.g., hydrazine, hydroxylamine, ammonia, organic nitro compounds (such as nitromethane, nitroethane, nitrobenzene, etc.), amines, amides, organic nitrites (such as methyl nitrite), nitriles (such as acetonitrile)), and a combination thereof.

Processes of the present disclosure may further comprise contacting at least a portion of the epoxidation reaction product comprising ethylene oxide with lean absorbent in the presence of an iodide-containing carboxylation catalyst in an ethylene oxide absorber to yield a fat absorbent stream comprising ethylene carbonate and/or ethylene glycol and a recycle gas stream comprising an alkyl iodide impurity and a vinyl iodide impurity. In the ethylene oxide absorber, the epoxidation reaction product is brought into intimate contact with lean absorbent in the presence of an iodide-containing carboxylation catalyst, and optionally a hydrolysis catalyst. Typically, the lean absorbent comprises at least 20 wt % water, and preferably comprises from 20 wt % to 80 wt % water. Preferably, the lean absorbent also comprises ethylene carbonate and/or ethylene glycol.

Suitably, an ethylene oxide absorber comprises an inlet that is in fluid communication with an outlet of an epoxidation reactor, an inlet through which lean absorbent is supplied, and an outlet that is in fluid communication with the recycle gas loop. An example of a suitable ethylene oxide absorber includes a column comprising a plurality of vertically stacked trays, which provide a surface area for the lean absorbent and the epoxidation reaction product to come into contact. Preferably, the column comprises at least 20 trays, more preferably at least 30 trays. Preferably the column comprises less than 100 trays, more preferably less than 70 trays, most preferably less than 50 trays. Suitably, the ethylene oxide absorber may be the sort of reactive absorber described in EP 2178815 or in co-pending application EP 14186273.0.

The temperature in the ethylene oxide absorber is preferably from 50° C. to 160° C., preferably from 80° C. to 150° C., more preferably from 80° C. to 120° C. This is higher than the temperature in a conventional process and is required to promote the carboxylation and hydrolysis reactions. Temperature higher than 160° C. is not preferred as this may reduce the selectivity of the ethylene oxide conversion to ethylene glycol. Both the epoxidation reaction product and the lean absorbent are preferably supplied to the ethylene oxide absorber at temperatures in the range from 50° C. to 160° C.

The pressure in the ethylene oxide absorber is from 1 to 4M Pa, preferably from 2 to 3 MPa. The preferred pressure is a compromise between lower pressures that require less expensive equipment (e.g. equipment having thinner walls) and higher pressures that increase absorption and reduce the volumetric flow of the gas, thereby reducing the size of equipment and piping.

The epoxidation reaction product stream supplied to the ethylene oxide absorber comprises carbon dioxide. However, it is possible that the epoxidation reaction product stream may contain insufficient carbon dioxide to achieve desired levels of carboxylation in the ethylene oxide absorber. Optionally, an additional source of carbon dioxide may be supplied to the ethylene oxide absorber, e.g. recycle carbon dioxide from a finishing reactor, carbon dioxide from a carbon dioxide recovery unit or, at start-up, carbon dioxide from an external source.

In the ethylene oxide absorber, the epoxidation reaction product is contacted with lean absorbent in the presence of an iodide-containing carboxylation catalyst and optionally a hydrolysis catalyst. Preferably, the epoxidation reaction product is contacted with lean absorbent in the presence of both an iodide-containing carboxylation catalyst and a hydrolysis catalyst. The carboxylation and hydrolysis catalysts may be homogeneous and/or heterogeneous. In one embodiment, the epoxidation reaction product is contacted with lean absorbent in the presence of both an iodide-containing carboxylation catalyst and a hydrolysis catalyst, and the lean absorbent comprises the catalysts.

Iodide-containing carboxylation catalysts suitable for use herein may be heterogeneous or homogeneous catalysts. Examples of suitable homogenous iodide-containing carboxylation catalysts include, but are not necessarily limited to, alkali metal iodides, such as potassium iodide, and organic phosphonium iodides or ammonium iodide salts such as tributylmethylphosphonium iodide, tetrabutylphosphonium iodide, triphenylmethylphosphonium iodide, and tributylmethylammonium iodide, and combinations thereof. Examples of suitable heterogeneous iodide-containing carboxylation catalysts include, but are not necessarily limited to, quaternary ammonium and quaternary phosphonium iodides immobilized on silica, quaternary ammonium and quaternary phosphonium iodides bound to insoluble polystyrene beads, and metal salts such as zinc salts immobilised on solid supports containing quaternary ammonium or quaternary phosphonium groups, such as ion exchange resins containing quaternary ammonium or quaternary phosphonium groups, and combinations thereof. Preferably the iodide-containing carboxylation catalyst is a homogeneous catalyst, most preferably an organic phosphonium iodide or alkali metal iodide.

Similarly, hydrolysis catalysts suitable for use herein may be heterogeneous or homogeneous catalysts. Examples of suitable homogenous hydrolysis catalysts include, but are not necessarily limited to, basic alkali metal salts, such as potassium carbonate, potassium hydroxide and potassium bicarbonate, and alkali metal metalates, such as potassium molybdate, and combinations thereof. Examples of suitable heterogenous hydrolysis catalysts include, but are not necessarily limited to, metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups, and combinations thereof.

A fat absorbent stream comprising ethylene carbonate and/or ethylene glycol is withdrawn from the ethylene oxide absorber via an outlet, preferably by withdrawing liquid from an outlet at the bottom of the ethylene oxide absorber. Preferably, at least 50% of the ethylene oxide entering the ethylene oxide absorber is converted in the ethylene oxide absorber. Preferably, at least 60%, more preferably at least 70%, even more preferably at least 80%, most preferably at least 90% of the ethylene oxide entering the ethylene oxide absorber is converted in the ethylene oxide absorber. The ethylene oxide may undergo carboxylation, providing ethylene carbonate. The ethylene oxide may undergo hydrolysis, providing ethylene glycol. Additionally, the ethylene carbonate that is produced from the ethylene oxide may undergo hydrolysis, providing ethylene glycol.

Optionally, a portion or all of the fat absorbent stream may be supplied to one or more finishing reactors (e.g., to provide further conversion of any ethylene oxide and/or ethylene carbonate that was not converted in the ethylene oxide absorber). Suitable finishing reactors may include a carboxylation reactor, a hydrolysis reactor, a carboxylation and hydrolysis reactor, and a combination thereof. Supply to one or more finishing reactors is preferred if a significant quantity (e.g. at least 1%) of ethylene oxide or ethylene carbonate is not converted to ethylene glycol in the ethylene oxide absorber.

That which is claimed is:

1. A process comprising:
    contacting at least a portion of a recycle gas stream comprising an alkyl iodide impurity and a vinyl iodide impurity with a first guard bed material to yield a partially treated recycle gas stream, wherein the first guard bed material comprises a first support material, and deposited on the first support material, silver in an amount of from 2% to 10% by weight;
    contacting at least a portion of the partially treated recycle gas stream with a second guard bed material to yield a treated recycle gas stream, wherein the second guard bed material comprises a second support material, palladium and gold; and
    contacting an epoxidation feed gas comprising ethylene, oxygen and at least a portion of the treated recycle gas stream with an epoxidation catalyst to yield an epoxidation reaction product comprising ethylene oxide.

2. The process of claim 1, further comprising:
    contacting at least a portion of the epoxidation reaction product comprising ethylene oxide with a lean absorbent in the presence of an iodide-containing carboxylation catalyst to yield a fat absorbent stream comprising ethylene carbonate and/or ethylene glycol and the recycle gas stream comprising the alkyl iodide impurity and the vinyl iodide impurity.

3. The process of claim 1, wherein silver is present in the first guard bed material in an amount of from 3% to 9% by weight.

4. The process of claim 1, wherein the first support material comprises alumina and is a spherical support material having a diameter of less than 2 mm.

5. The process of claim 1, wherein palladium is present in the second guard bed material in an amount of from 0.1% to 3% by weight.

6. The process of claim 1, wherein gold is present in the second guard bed material in an amount of from 0.1% to 3% by weight.

7. The process of claim 1, wherein the second support material comprises silica.

8. The process of claim 1, wherein the partially treated recycle gas stream comprises no more than 6 ppbv of alkyl iodide.

9. The process of claim 1, wherein the partially treated recycle gas stream comprises no more than 1 ppbv of alkyl iodide.

10. The process of claim 1, wherein the treated recycle gas stream comprises no more than 20 ppbv of vinyl iodide.

11. The process of claim 1, wherein the treated recycle gas stream comprises no more than 1 ppbv of vinyl iodide.

12. The process of claim 1, wherein the treated recycle gas stream comprises no more than 1 ppbv of alkyl iodide and no more than 1 ppbv of vinyl iodide.

13. A reaction system for the production of ethylene carbonate and/or ethylene glycol comprising:
    a recycle gas loop fluidly connected to a source of ethylene and oxygen;
    an epoxidation reactor comprising an epoxidation catalyst, an inlet, and an outlet, wherein the inlet of the epoxidation reactor is fluidly connected to the recycle gas loop;
    an ethylene oxide absorber comprising an iodide-containing carboxylation catalyst, an inlet, and an outlet, wherein the outlet of the epoxidation reactor is fluidly connected to the inlet of the ethylene oxide absorber, the outlet of the ethylene oxide absorber is fluidly connected to the recycle gas loop, and the ethylene oxide absorber is configured to produce a recycle gas stream comprising a vinyl iodide impurity and an alkyl iodide impurity and a fat absorbent stream comprising ethylene carbonate and/or ethylene glycol;
    a first guard bed system comprising an inlet, an outlet and one or more guard bed vessels comprising a first guard bed material that comprises a first support material, and deposited on the first support material, silver in an amount of from 2% to 10% by weight, wherein the inlet of the first guard bed system is fluidly connected to the recycle gas loop, and the first guard bed material is configured to remove at least a portion of the alkyl iodide impurity from at least a portion of the recycle gas stream to yield a partially treated recycle gas stream; and
    a second guard bed system comprising an inlet, an outlet and one or more guard bed vessels comprising a second guard bed material that comprises a second support material, palladium and gold, wherein the inlet of the second guard bed system is fluidly connected to the outlet of the first guard bed system, the outlet of the second guard bed system is fluidly connected to the recycle gas loop, and the second guard bed material is configured to remove at least a portion of the vinyl iodide impurity from at least a portion of the partially treated recycle gas stream.

14. The reaction system of claim 13, further comprising a carbon dioxide absorber fluidly connected to the recycle gas loop.

15. The reaction system of claim 13, wherein the first guard bed system, the second guard bed system or both comprise two or more guard bed vessels.

* * * * *